United States Patent [19]

Leadbeater et al.

[11] Patent Number: 5,250,557
[45] Date of Patent: Oct. 5, 1993

[54] MICROBICIDAL COMPOSITIONS

[75] Inventors: Andrew Leadbeater, Great Dunmow, England; Bernhard Steck, Muntelier; Robert Nyfeler, Basel, both of Switzerland

[73] Assignee: Ciba-Geigy Corporation, Ardsley, N.Y.

[21] Appl. No.: 792,845

[22] Filed: Nov. 15, 1991

[30] Foreign Application Priority Data

Nov. 20, 1990 [CH] Switzerland .................. 3682/90

[51] Int. Cl.$^5$ .................. A01N 43/36; A01N 43/64
[52] U.S. Cl. .................. 514/383; 514/422
[58] Field of Search .................. 514/383, 422

[56] References Cited

U.S. PATENT DOCUMENTS 4,705,800  11/1987  Nyfeler et al. .................. 514/422
4,940,721   7/1990  Nevill .................. 514/383

FOREIGN PATENT DOCUMENTS 2098607  11/1982  United Kingdom .

OTHER PUBLICATIONS

Nyfeler et al., C.A., vol. 107, (1987), 107:2683b.
Mittermeier et al., C.A., vol. 114, (1991), 114:37779j.
2244 Research Disclosure, (Jan. 1989), No. 29748, "Combinations of Microbiocides for Improved Plant Protection in Pomefruit".
2244 Research Disclosure, (Jan. 1989), No. 29718, "Fungicidal Mixtures of CGA 169374 with Other Fungicides for Controlling Cereal Diseases".

*Primary Examiner*—Allen J. Robinson
*Attorney, Agent, or Firm*—Edward McC. Roberts; Marla J. Mathias

[57] ABSTRACT

The combination of the plant microbicide 4-(2,2-difluoro-1,3-benzodioxol-7-yl)-1H-pyrrole-3-carbonitrile with the plant microbicide 1-{2-[2-chloro-4-(4-chlorophenoxy)phenyl]-4-methyl-1,3-dioxolan-2-ylmethyl}-1H-1,2,4-triazole results in a synergistically increased effect in the control of plant diseases. Microbicidal compositions based on such combinations are suitable for treating crops of plants and natural products of vegetable and animal origin, and for seed treatment.

10 Claims, No Drawings

MICROBICIDAL COMPOSITIONS

The present invention relates to microbicidal mixtures which have a synergistically enhanced action against plant diseases and against infestation with microorganisms on propagation stock of plants or on other vegetable or animal material, and to processes for applying such mixtures, in particular for seed dressing.

The invention particularly relates to the control, or prevention, of diseases in cereal crops.

It has been found that a combination of component I), 4-(2,2-difluoro-1,3-benzodioxol-7-yl)-1H-pyrrole-3-carbonitrile, of the formula 1

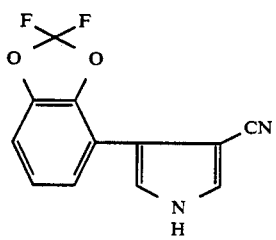

with component II), 1-{2-[2-chloro-4-(4-chlorophenoxy)phenyl]-4-methyl-1,3-dioxolan-2-ylmethyl}-1H-1,2,4-triazole, of the formula II

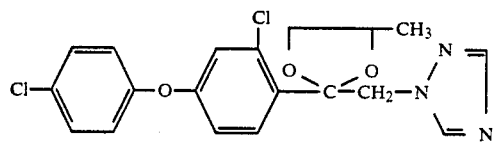

or with a salt thereof results in a synergistically enhanced activity in the control and prevention of plant diseases.

EP-A-206 999 describes the compound of the formula I as a fungicidal active ingredient. It is distinguished, in particular, as a contact fungicide.

British Patent Application 2 098 607 describes the compound of the formula II as a fungicidal active ingredient. The action of this triazole derivative is based on the inhibition of ergosterin biosynthesis.

The abovementioned salts of the compound of formula II can be prepared by reacting the base with acids.

The acids which can be used for preparing salts of the formula II include: hydrohalic acid such as hydrofluoric acid, hydrochloric acid, hydrobromic acid or hydroiodic acid, and also sulfuric acid, phosphoric acid, nitric acid, and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term salts also comprises metal complexes of the basic component II. These complexes are composed of the basic organic molecule and an inorganic or organic metal salt, for example the halides, nitrates, sulfates, phosphates, acetates, trifluoroacetates, trichloroacetates, propionates, tartrates, sulfonates, salicylates, benzoates and the like, of the elements of the second main group of the Periodic Table such as calcium and magnesium, and of the third and fourth main group, such as aluminium, tin or lead, and of the first to eighth auxiliary group such as chromium, manganese, iron, cobalt, nickel, copper, zinc, and the like. Preferred elements are auxiliary group elements of the 4th period. The metals may exist in different valence states. The metal complexes can be mononuclear or polynucelar, i.e. they can contain one or more parts of the organic molecule as ligands.

It is known to a person skilled in the art that the action of a fungicide can be substantially increased or broadened by adding another fungicide having a different activity spectrum.

Surprisingly, however, it has been found that the combination of the active ingredients I and II results in a quite unexpectedly enhanced action against seed-borne and soil-borne fungi. The increase in action achieved with the combination according to the invention is significantly greater than the activity to be expected by the two individual components, i.e. the activity is enhanced synergistically.

The present invention makes it possible to dress seeds with lower amounts of biocides than is known from the prior art and therefore represents a material enrichment of the art.

The invention not only relates to the use of mixtures of components I and II for treating seeds but also to the application of the individual pure components in immediate succession.

Advantageous mixing ratios of the two active substances are I:II = 10:1 to 1:100, in particular I:II = 5:1 to 1.60 and very particularly I:II = 3:1 to 1:12. Other advantageous mixing ratios are I:II = 5:2 to 2:5, or 3:5, 1:1, 3:20, 3:40.

The combination of the active components I and II according to the invention effects a useful contact action as well as systemic action and long term action in the control of the seed- and soil-borne plant diseases. The microorganisms on the storage goods and on the propagation material, in particular on seeds, are destroyed by the combinations according to the invention, and developing plants are protected against attack by the soil-borne microorganisms.

The mixtures according to the invention are effective against phytopathogenic fungi which belong to the following classes: Ascomycetes (for example the genera Erysiphe, Sclerotinia, Monilinia, Helminthosporium [=Drechslera], Mycosphaerella, Pyrenophora); Basidiomycetes (for example the genera Puccinia, Tilletia, Rhizoctonia); Fungi imperfecti (for example the genera Gerlachia [=Fusarium], Septoria, Phoma, Alternaria). The combinations according to the invention are particularly effective in seed treatment (fruit, tubers, grains), and the action against *Gerlachia nivalis* [=*Fusarium nivale*] on wheat is particularly pronounced. However, they are also suitable for direct treatment of the soil or of other parts of the plant. They are well tolerated by plants, and they are ecologically acceptable.

The mixture according to the invention is usually employed together with the adjuvants customary in formulation technology. The active components of the formula I or II are processed in known manner to give, for example, emulsifiable concentrates, spreadable pastes, directly sprayable or dilutable solutions, dilute emulsions, wettable powders, soluble powders, dusts, granules, and also for encapsulation in, for example, polymeric substances. The application methods, such as spraying, misting, atomising, broadcasting, brushing or pouring, and the nature of the composition are adapted to suit the intended aims and the prevailing circumstances. In general, favourable rates of application are 0.0005 to not more than 0.5 kg, in particular 0.001–0.01 kg of each active ingredient I and II per 100 kg of material to be protected. However, the application conditions depend essentially on the nature (surface area, consistency, moisture content) of the material and on its environmental factors.

Within the scope of the present invention, storage goods which can be protected with the mixture according to the invention, in particular plant propagation material, especially seeds, will be understood as meaning natural substances of vegetable and/or animal origin and their processing products for which long-term protection is desired, for example the plants and parts thereof, which are mentioned below (stalks, leaves, tubers, seeds, fruits, grains) which have been taken from the natural life cycle and which exist in the freshly harvested state or in processed form (pre-dried, moistened, comminuted, ground, pressed, roasted, etc.). Also falling within the scope of the invention is the protection of timber, whether in the form of crude timber (construction timber, electricity pylons, barriers) or in the form of finished articles (furniture, objects made from wood). Natural products of animal origin which are to be preserved, for example hides, furs, hairs and the like, likewise fall within the scope of the invention.

Target crops within the scope of this invention are, for example, the following plant species: cereals; (wheat, barley, rye, oats, rice, sorghum, maize and related species); beet (sugar and fodder beet); legumes: (beans, lentils, soya beans, peas); oil crops: (oilseed rape, mustard, poppy, sunflowers); cucurbits: (cucumbers, pumpkin, melons); fibre plants: (cotton, flax); various vegetables: (lettuce, cabbages, spinach, carrots, onions, tomatoes, potatoes, capsicum); ornamentals: (tulips, daffodils, dahlias, chrysanthemums and other flowers), and culinary herbs and their seeds.

A preferred method of applying the mixture according to the invention consists in spraying or wetting the plant material with a liquid preparation, or mixing the plant material with a solid preparation of the active ingredients. The invention also relates to these preservation methods and to the wood or storage goods or plant propagation material, treated with this mixture of I and II. The last-mentioned term "plant propagation material" comprises generative plant material such as seeds and vegetative plant material such as cuttings and tubers (for example potatoes).

The active ingredients of the formulae I and II are used according to the invention in the form of compositions and can be employed together with, if appropriate, other carriers customary in formulation technology, surfactants or other additives which promote the application of the active ingredients.

Suitable carriers and additives can be solid or liquid and correspond to the substances which are expedient in formulation technology, for example natural or regenerated mineral substances, solvents, dispersants, wetting agents, tackifiers, thickeners, binders or fertilizers.

A preferred method of applying a mixture of active ingredients of the formulae I and II or of an (agro)-chemical composition which contains these compounds is foliar application. In this context, the number of applications and the rate of application depend on the risk of infestation by the pathogen in question (fungal species).

However, the active ingredient mixture can also be taken up by the plant via the roots through the soil (systemic action) by drenching the locus of the plant with a liquid preparation or by incorporating the substances in the soil in solid form, for example in the form of granules (soil application). In a particularly preferred method, seed kernels, tubers, fruits or other plant material to be protected (for example also wood) can be coated with the mixture of the compounds of the formulae I and II, either by impregnating the material with a liquid preparation of the active ingredients or by applying a layer of a solid preparation. Moreover, other types of application are possible in special cases, for example the targeted treatment of plant cutting or twigs which are intended for propagation.

In this context, the compounds of the formulae I and II are employed in unmodified form or, preferably, together with the adjuvants customary in formulation technology, and they are therefore processed in known manner to give, for example, emulsifiable concentrates, spreadable pastes (for example for the protection of wood), directly sprayable or dilutable solutions, dilute emulsions, wettable powders, soluble powders, dusts, granules, and also encapsulations, for example in polymeric substances. The application methods such as spraying, misting, dusting, broadcasting, brushing on or pouring as well as the nature of the compositions are selected to suit the intended aims and the prevailing circumstances. In the case of field treatment, favourable rates of application are generally 5 g to 5 kg of active ingredient (a.i.) of the formulae I and II per ha; preferably 10 g to 2 kg of a.i./ha, particularly preferably 20 g to 600 g of a.i./ha.

The formulations, i.e. the compositions, preparations or combinations containing the active ingredients of the formulae I and II, as well as, if appropriate, a solid or liquid additive, are prepared in a known manner, for example by intimately mixing and/or grinding the active ingredients with extenders, for example with solvents, solid carriers and, if appropriate, surface-active compounds (surfactants).

Suitable solvents are: aromatic hydrocarbons, in particular the fractions $C_8$ to $C_{12}$, such as xylene mixtures or substituted naphthalenes, phthalic esters such as dibutyl or dioctyl phthalate, aliphatic hydrocarbons such as cyclohexane or paraffins, alcohols and glycols as well as their ethers and esters, such as ethylene glycol monomethyl ether, ketones such as cyclohexanone, strongly polar solvents such as N-methyl-2-pyrrolidone, dimethyl sulfoxide or dimethylformamide, and, if appropriate, epoxidized vegetable oils or soybean oil; or water.

Solid carriers which may be used, for example for dusts and dispersible powders, are calcite, talc, kaolin, montmorillonite or attapulgite, highly-disperse silica or absorptive polymers. Possible particulate, adsorptive carriers for granules are pumice, crushed brick, sepiolite or bentonite, and possible nonsorbent carrier materials are calcite or dolomite. Suitable surface-active compounds are non-ionic, cationic and/or anionic surfactants having good emulsifying, dispersing and wetting properties, depending on the nature of the active ingredients of the formulae I and II to be formulated. Surfactants will also be understood as meaning mixtures of surfactants.

The surfactants customarily employed in formulation technology are described, inter alia, in the following publications:

"McCutcheon's Detergents and Emulsifiers Annual", MC Publishing Corp., Glen Rock, N.J., 1988.

M. and J. Ash, "Encyclopedia of Surfactants", Vol. I-III, Chemical Publishing Co., New York, 1980-1981.

Furthermore, particularly useful adjuvants which enhance application are natural or synthetic phospholipids from the series of the cephalins and lecithins, for example phosphatidylethanolamine, phosphatidylserine, phosphatidylglycerine or lysolecithin.

As a rule the agrochemical compositions contain 0.1 to 99%, in particular 0.1 to 95%, of active substance of the formula I, 99.9 to 1%, in particular 99.9 to 5%, of a solid or liquid additive, and 0 to 25%, in particular 0.1 to 25%, of a surfactant.

Whereas commercial products will preferably be formulated as concentrates, the end user will normally use dilute formulations.

The present invention also relates to such (agro)-chemical compositions.

The examples which follow are intended to illustrate the invention, "active ingredient" being understood as meaning a mixture of compound I and compound II in a particular mixing ratio of 10:1 to 1:10.

| Wettable powder | a) | b) | c) |
| --- | --- | --- | --- |
| Active ingredient I:II = [3:2 (a), 1:9 (b), 1:4 (c)] | 25% | 50% | 75% |
| Sodium ligninsulfonate | 5% | 5% | — |
| Sodium lauryl sulfate | 3% | — | 5% |
| Sodium diisobutylnaphthalenesulfonate | — | 6% | 10% |
| octylphenol polyethylene glycol ether (7-8 mol of ethylene oxide) | — | 2% | — |
| highly disperse silica | 5% | 10% | 10% |
| kaolin | 62% | 27% | — |

The active ingredient is mixed thoroughly with the additives and the mixture is ground thoroughly in a suitable mill affording wettable powders which can be diluted with water to give suspensions of any desired concentration. Such slurries can be used for carrying out foliar treatments on crops of plants and also for wet- or moist-dressing material which can be propagated, for example grain seeds or tubers of plants.

| Emulsifiable concentrate | |
| --- | --- |
| Active ingredient (I:II = 2:3) | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any desired concentration can be prepared from this concentrate by dilution with water, and can be employed in crop protection and in the protection of wood.

| Dusts | a) | b) |
| --- | --- | --- |
| Active ingredient (I:II = 4:1 and 1:1) | 5% | 8% |
| talc | 95% | — |
| kaolin | — | 92% |

Ready-to-use dusts are obtained by mixing the active ingredient with the carrier and grinding the mixture in a suitable mill. Such powders can be used for dry-dressing seeds.

| Extruder granules | |
| --- | --- |
| Active ingredient (I:II = 3:10) | 13% |
| Sodium ligninsulfonate | 2% |
| carboxymethylcellulose | 1% |
| kaolin | 84% |

The active ingredient is mixed with the additives, and the mixture is ground and moistened with water. This mixture is extruded and subsequently dried in a stream of air.

| Coated granules | |
| --- | --- |
| Active ingredient (I:II = 3:5) | 8% |
| polyethylene glycol (MW 200) | 3% |
| kaolin | 89% |
| (MW = molecular weight) | |

In a mixer, the kaolin which has been moistened with polyethylene glycol is coated uniformly with the finely ground active ingredient to give non-dusty coated granules.

| Suspension concentrate | |
| --- | --- |
| Active ingredient (I:II = 3:5) | 40% |
| propylene glycol | 10% |
| nonlyphenol polyethylene glycol ether (15 mol of EO) | 6% |
| Sodium ligninsulfonate | 10% |
| carboxymethylcellulose | 1% |
| silicone oil (as 75% aqueous emulsion) | 1% |
| water | 32% |

The finely ground active ingredient is mixed intimately with the additives. In this manner, a suspension concentrate is obtained from which suspensions of any desired dilution can be prepared by addition of water. such dilute suspensions can be used for treating live plants or products of vegetable or animal origin by spraying, pouring-on or immersion and for protecting them against infection by microorganisms.

BIOLOGICAL EXAMPLES

Fungicides always have a synergistic effect if the fungicidal activity of the combined formulation is greater than the sum of the activity of the individually applied fungicides.

The expected activity E for a given combined formulation, e.g. consisting of two fungicides, obeys the COLBY formula and can be calculated as follows (COLBY, L.R. "Calculating synergistic and antagonistic responses of a herbicide combination", Weeds 15, pp. 20-22), (LIMPEL et al., 1062 "Weeds control by . . . certain combinations", Proc. NEWCL, Vol. 16, pp. 48-53): (g of a.i./ha=grams of active ingredient per hectare).

$X$=percentage activity of fungicide I at a rate of application of p g of a.i./ha $Y$=percentage activity of fungicide II at a rate of application of q g of a.i./ha $E$ = expected activity of fungicides I+II at a rate of application of p+q of a.i./ha then according to Colby:

$$E = X + Y - \frac{X \cdot Y}{100}$$

If the actually observed activity (O) is greater than that calculated, then the activity of the combined formulation is greater than additive, i.e. there is synergism.

FUNGICIDAL ACTION AGAINST THE PATHOGEN OF *GERLACHIA NIVALIS* ON SEEDS OF WINTER WHEAT

Winter wheat (cv. Eiger) which is infected with *Gerlachia nivalis* is harvested from the field. The malt agar test reveals that 24% of the seeds are infected. This seed is treated either with one of the active ingredients I or II or with mixtures of the active ingredients as shown in the following table. The active components are first dispersed in water and this dispersion is sprayed onto the seed which is on a rotating disc. This procedure corresponds to conditions found in practice. Untreated seeds from the same origin are used for comparison purposes.

Batches of 100 grains are sown in seed dishes (45×35×10 cm) in sterile field soil at a depth of 2 cm. Three replications of the test are run. The seed dishes are kept moist for 21 days at 5° C. with the exclusion of light. They are then transferred to a control-environment cabinet with illumination (day/night: 16/8 hours; 10° C.) where the plants emerge. Germination does not take place in the case of those grains which are heavily infected with *G. nivalis*. After 10 days, the dishes are covered with a plastic film and maintained at 10° C., without light. Due to the high atmospheric humidity under the cover, fungal mycelium becomes apparent on the stem base of those plants which are infected with *G. nivalis*. 59 days after sowing, the number of existing plants and the number of infected plants is determined. The sum of the number of non-germinated grains and the number of infected plants forms the total infection rate. This rate is compared with the total infection rate in the comparison seed dishes with untreated seeds and expressed as the total percentage infection rate.

For example, at a rate of application of 1.5 g of a.i/100 kg of seed, using component I only, an effect of only 58% is achieved. Component II achieves an effect of only 27% at a rate of application of 2.5 g of a.i./100 kg of seed. A mixture of these two components, calculated by COLBY's formula, would give the following expected effect (E):

$$E = 58 + 27 - \frac{58 \cdot 27}{100} = 69\% \text{ effect}$$

However, as can be shown in the Table below, the effect of 78%, which has been achieved in practice with this test (No. 10), is much higher than expected.

As can be seen from the Table below, mixtures of the compounds I and II exhibit a substantially enhanced activity when compared with the individual applications of components I (test no. 2, 3 and 4) and II (test no. 5, 6, 7 and 8).

TABLE

| Treatment | g of active ingredient/ 100 kg of seed | | Total infestation rate (%) | Effect E (calculated) (COLBY) | Effect O (found) |
|---|---|---|---|---|---|
| | Component I | Component II | | | |
| 1. Comparison | — | — | 100 | — | — |
| 2. | 0.38 | — | 64 | — | 36 |
| 3. | 0.75 | — | 52 | — | 48 |
| 4. | 1.5 | — | 42 | — | 58 |
| 5. | — | 2.5 | 73 | — | 27 |
| 6. | — | 5.0 | 53 | — | 47 |
| 7. | — | 10 | 39 | — | 61 |
| 8. | — | 20 | 25 | — | 75 |
| 9. | 0.38 | 2.5 | 41 | 53 | 59 |
| 10. | 1.5 | 2.5 | 22 | 69 | 78 |
| 11. | 1.5 | 5.0 | 17 | 78 | 83 |
| 12. | 1.5 | 10 | 10 | 84 | 90 |
| 13. | 0.38 | 20 | 10 | 84 | 90 |
| 14. | 0.75 | 20 | 8 | 87 | 92 |
| 15. | 1.5 | 20 | 6 | 89 | 94 |

As can be seen from the table, treatments 9–15, in which the mixing ratios of the components I and II were varied within a wide range, showed a markedly increased, i.e. synergistic, effect.

A comparably enhanced increased, i.e. synergistic, effect has been found against *Gerlachia nivalis* on barley and rye, against *Pyrenophora graminea* and *P. teres* on barley, against *Tilletia caries* on wheat, and against other seed-and soil-borne pathogens.

What is claimed is:

1. A composition for controlling or preventing infections by plant pathogenic fungi, containing a synergistic plant pathogenic fungicidally effective amount of a mixture of two active ingredient components I)and II), component I) being 4-(2,2-difluoro-1,3-benzodioxol-7-yl)-1H-pyrrole-3-carbonitrile of the formula

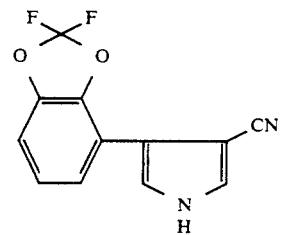

component II) being 1-{2-[2-chloro-4-(4-chlorophenoxy)-phenyl]-4-methyl-1,3-dioxolan-2-ylmethyl}-1H-1,2,4-triazole of the formula

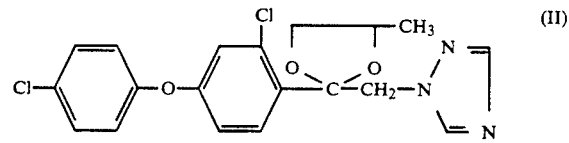

or a salt thereof, the synergistic ratio by weight of I):II) being from 1:1.66 to 1:52.63, together with a suitable carrier.

2. A method of controlling or preventing an infection of a plant or a part of a plant by plant pathogenic fungi, which comprises treating said plant, which is already infected or is liable to be infected, or said part of a plant, which is already infected or is liable to be infected, or the locus of said plant, with a synergistic fungicidally effective amount of a composition according to claim 1.

3. A method as claimed in claim 2, wherein said plant or said part of a plant is a plant propagation material.

4. A method as claimed in claim 3, wherein said plant propagation material is a seed.

5. A method according to claim 2, wherein the active ingredients are applied in direct succession.

6. A method of protecting materials of animal or vegetable origin against attack by plant pathogenic fungi, which comprises treating said materials with a synergistic fungicidally effective amount of a composition according to claim 1.

7. A method according to claim 6, wherein said materials of animal or vegetable origin is a storage good or timber.

8. A method according to claim 6, wherein said materials are storage goods of vegetable origin harvested from the natural life cycle.

9. A plant propagation material, the plants grown from which are protected against harmful plant fungi occurring in the soil, comprising a plant propagation material coated with a synergistic fungicidally effective amount of a composition according to claim 1.

10. The plant propagation material of claim 9, wherein the plant propagation material is a seed.

* * * * *